United States Patent [19]
Horrobin et al.

[11] Patent Number: 5,378,732
[45] Date of Patent: Jan. 3, 1995

[54] METHOD OF REDUCING THE RATE OF REOCCLUSION OF ARTERIES

[75] Inventors: David F. Horrobin; John C. M. Stewart, both of Guildford, England

[73] Assignee: Scotia Holdings PLC, Surrey, England

[21] Appl. No.: 981,116

[22] Filed: Nov. 25, 1992

[30] Foreign Application Priority Data

Dec. 2, 1991 [GB] United Kingdom ............... 9125602

[51] Int. Cl.$^6$ ............................................. A61K 31/20
[52] U.S. Cl. .................................................. 514/560
[58] Field of Search ........................ 514/549, 560, 824

[56] References Cited

U.S. PATENT DOCUMENTS

| | | | |
|---|---|---|---|
| 4,526,902 | 7/1985 | Rubin | 514/560 |
| 4,780,456 | 10/1988 | Pistolesi | 514/560 |
| 4,920,098 | 4/1990 | Cotter et al. | 514/2 |
| 5,059,622 | 10/1991 | Sears | 514/560 |

OTHER PUBLICATIONS

Database WPIL, Week 8534, Derwent Publications Ltd., London, GB; AN 85-207768 & JP-A-60 132 916 (Nisshin Oil Mills KK), Abstract (1985).

Lechleitner et al., Wiener Medizinische Wochenschrift, vol. 140, No. 10, Jun. 1990 pp. 277-278, "Medikamentöse Prophylaxe nach koronarer Bypassoperation oder PTCA" (1990).

Aoki et al., Prostaglandins Leukotriens and Essential Fatty Acids, vol. 37, No. 2, pp. 89-95, "Acute Effects of unsaturated fatty etc." (1989).

European Search Report of European Application No. 92310807.0 (May 12, 1993).

Passwater, Richard A., "Evening Primrose Oil" (1981) pp. 1-11.

Primary Examiner—Raymond J. Henley, III
Attorney, Agent, or Firm—Nixon & Vanderhye

[57] ABSTRACT

Gamma-linolenic acid and/or dihomo-gamma-linolenic acid is used in a medicament for reducing the rate of reocclusion of an artery from which an occlusion or other blockage has been removed, or for preventing occlusion of peripheral or coronary arteries. The medicament may also comprise eicosapentaenoic acid.

10 Claims, No Drawings

METHOD OF REDUCING THE RATE OF REOCCLUSION OF ARTERIES

The present invention relates to a method of inhibiting reocclusion of arteries, and to the use of GLA and/or DGLA for the preparation of a medicament for use in said method.

Arteries frequently become partially or totally occluded by atherosclerosis. Over the past twenty years, many methods have been developed aimed at clearing obstructions and allowing the tree flow of blood. Such methods have included direct surgical techniques, the introduction of balloons, or other devices, attached to catheters which, when expanded at an appropriate site, partially or completely clear the blockage, and the use of lasers to blast away the occlusion.

Unfortunately, however, the artery does not always remain open. Sometimes it becomes blocked again very quickly because of a thrombosis. More frequently it closes after weeks, months or even years as a result of the redevelopment of the atherosclerosis. These closures are known as reocclusions. Depending on various factors, such as the technique used, may arteries are found to reocclude. Typically, 20–40% of opened arteries close again.

Thus, it would be highly advantageous if reocclusion could be prevented, and especially, if initial occlusion can be prevented. The benefits to patients and the saving of costs would be considerable.

Many drugs have been tested for the prevention of reocclusion, but the results have thus tar been largely disappointing. Fish oils, containing the fatty acids eicosapentaenoic acid and docosahexaenoic acid have been tested and occasionally been found to be beneficial, but even the positive effects have been small. There is therefore a great need for new agents in this field.

The essential fatty acid γ-linolenic acid is known to be converted within the body to dihomo-γ-linolenic acid, a precursor of the prostaglandin $PGE_1$, which is a powerful anti-aggregatory agent which inhibits platelet aggregation. However, inhibition of the aggregation of platelets alone is unlikely to be effective. EFA, which has a similar effect on platelet aggregation to GLA, has given equivocal and inconsistent results in tests of its ability to prevent reocclusion. GLA has additional cardiovascular benefits in that it, probably through its conversion to $PGE_1$, lowers cholesterol levels and causes dilation of small blood vessels.

Surprisingly, it has been found that administration of γ-linolenic acid to patients after they have undergone angioplasty, or any other equivalent method of reopening blood vessels, results in an impressive reduction of the rate of reocclusion in these patients. Although DGLA has not been tested directly, it is likely that it would be as efficacious as GLA. This is because the administration of GLA to humans is rapidly followed by an elevation of DGLA levels because of rapid conversion of the GLA.

Thus, in a first aspect, there is provided a method of inhibiting reocclusion of an artery from which an occlusion has been removed by administering a composition comprising an effective, non-toxic amount of γ-linolenic acid or dihomo-γ-linolenic acid.

The invention also embraces a method for preventing occlusion of peripheral or coronary arteries by administering a composition comprising an effective, non-toxic amount of γ-linolenic acid or dihomo-γ-linolenic acid.

The γ-linolenic acid or dihomo-γ-linolenic acid may be administered in the form of any appropriate derivative such as the free acid, the potassium, lithium or other alkali metal salt, a salt of another metal, eg. zinc, calcium or magnesium, the mono-, di- or triglyceride, ethyl or any other appropriate esters, phospholipids, amides or any other derivative which will lead to elevation of γ-linolenic acid or dihomo-γ-linolenic acid and/or its metabolites in the body.

In a second aspect of the invention there is provided use of γ-linolenic acid or dihomo-γ-linolenic acid for the manufacture of a medicament for the inhibition of reocclusion of an artery from which an occlusion or other blockage has been removed.

The invention also embraces the use of γ-linolenic acid or dihomo-γ-linolenic acid for the manufacture of a medicament for preventing occlusion of peripheral or coronary arteries.

Furthermore, it has been found that the compositions of the present invention which further comprise the fatty acid eicosapentaenoic acid (which has been shown to have little effect in the prevention of reocclusion when administered on its own), are particularly effective in preventing reocclusion.

Administration of capsules containing γ-linolenic acid in combination with eicosapentaenoic acid, over a period of up to 1 year, to patients who have had an occlusion of the femoral artery removed by balloon angioplasty, has been found to result in a significant reduction of the reocclusion rate. There is every reason to believe that such reductions in the reocclusion rate will also be observed on administration of compositions of the invention following coronary angioplasty, as well as methods of reopening blood vessels other than angioplasty. Since GLA, optionally with EPA is able to prevent reocclusion, it is also likely to be able to prevent occlusion in the first place and such prevention of occlusion of peripheral or coronary arteries is within the scope of this invention.

In the compositions of the present invention, it is preferred that γ-linolenic acid or dihomo-γ-linolenic acid is administered in a dose of from 1 mg to 10 g/day, preferably 100 mg to 4 g/day, particularly 500 mg to 2 g/day. Such compositions may optionally further contain eicosapentaenoic acid, as stated above, the additional dose of eicosapentaenoic acid being from 1 mg to 10 g/day, preferably 100 mg to 4 g/day, particularly 500 mg to 2 g/day. In particularly preferred compositions, the amount of eicosapentaenoic acid in the pharmaceutical compositions is relatively smaller compared to the amount of γ-linolenic acid or dihomo-γ-linolenic acid. The ratio of γ-linolenic acid:eicosapentaenoic acid is typically from 20:1 to 3:1.

The γ-linolenic acid or dihomo-γ-linolenic acid, either singly or in combination, further optionally in combination with eicosapentaenoic acid, may be administered orally in any appropriate dosage form, such as soft or hard gelatin capsules, which may or may not be enteric-coated, tablets, whips, liquids, internal formulations or any other appropriate formulation known to those skilled in the art. The medicaments may also be administered topically, parenterally by injection (intravenous, intradermal or subcutaneous), infusion or any other appropriate route, rectally or vaginally.

Soft or hard gel gelatin capsules, enteric coated or not, for example, may contain 100, 200, 300 or 600 mg of γ-linolenic acid in any appropriate form, optionally with an appropriate amount of eicosapentaenoic acid in any appropriate form.

Further examples include an emulsion for intravenous administration which may contain 100 mg of γ-linolenic acid/ml optionally with 5-30 mg of eicosapentaenoic acid/ml, a cream for topical administration which may contain 1-20% of triglyceride γ-linolenic acid, while a suppository for rectal administration or a pessary for vaginal administration may contain 1 g of γ-linolenic acid in an appropriate formulation.

The invention is further illustrated by the following, non-limiting example.

EXAMPLE

Patients with occlusion of the femoral artery were entered into the study. The occlusion was treated by balloon angioplasty. One week prior to the angioplasty patients commenced treatment with either 6 capsules/day of placebo or 6 capsules/day or 270 mg of γ-linolenic acid and 45 mg of eicosapentaenoic acid. Treatment with active drug or placebo then continued for one year after angioplasty. Blood flow in the femoral artery was monitored before angioplasty, 1-2 days after angioplasty and at 6 months and 12 months using Doppler flowmetry. If symptoms suggesting reocclusion developed at any time during the study, Doppler flowmetry was performed and if occlusion was suspected this was confirmed by performing an angiogram.

60 patients entered the study and 46 have completed one year. 30 patients received active and 30 placebo treatment.

Of the 46 patients who have completed one years treatment at the time of writing, 23 were assigned to active treatment, and 23 to placebo.

In the patients in the active group, the arteries of 19 patients have remained open, while 4 have reoccluded. In the placebo group, the arteries of 12 patients have remained open, while 11 have reoccluded.

This is a significant reduction of the reocculsion rate, showing that γ-linolenic acid in combination with eicosapentaenoic acid is highly effective in preventing reocclusion after femoral angioplasty.

We claim:

1. A method of reducing the rate of reocclusion of an artery from which an atherosclerotic occlusion has been removed in a patient in need thereof which comprises administering to said patient a composition comprising an effective, non-toxic amount of γ-linolenic acid and/or dihomo-γ-linolenic acid.

2. A method according to claim 1, wherein γ-linolenic acid and/or dihomo-γ-linolenic acid is administered in a dose range of from 1 mg to 10 g/day.

3. A method according to claim 2, wherein the γ-linolenic acid and/or dihomo-γ-linolenic acid is administered in a dose range from 100 mg to 4 g/day.

4. A method according to claim 3, wherein the γ-linolenic acid and/or dihomo-γ-linolenic acid is administered in a dose range from 500 mg to 2 g/day.

5. A method according to claim 1, wherein the composition further comprises eicosapentaenoic acid.

6. A method according to claim 5, wherein eicosapentaenoic acid is administered in an amount of from 1 mg to 10 g/day.

7. A method according to claim 6, wherein eicosapentaenoic acid is administered in an amount of from 100 mg to 4 g/day.

8. A method according to claim 7, wherein eicosapentaenoic acid is administered in an amount of from 500 mg to 2 g/day.

9. A method according to claim 5, wherein the composition comprises a relatively smaller amount of eicosapentaenoic acid than of γ-linolenic acid and/or dihomo-γ-linolenic acid.

10. A method according to claim 9, wherein the composition comprises a ratio of γ-linolenic acid and/or dihomo-γ-linolenic acid to eicosapentaenoic acid of from 20:1 to 3:1.

* * * * *